United States Patent
Carlson

[19]

[11] Patent Number: 6,152,891
[45] Date of Patent: Nov. 28, 2000

[54] HUMAN SHOULDER BRACE

[76] Inventor: Greg Carlson, 2320 54th St., San Diego, Calif. 92105

[21] Appl. No.: 09/377,534

[22] Filed: Aug. 19, 1999

[51] Int. Cl.[7] .............................. A61F 5/00; A61F 13/00

[52] U.S. Cl. .................................. 602/4; 602/20; 602/60; 602/61

[58] Field of Search ................................ 2/459, 460, 461, 2/44, 45; 602/4, 5, 20, 60, 61, 62, 63

[56] References Cited

U.S. PATENT DOCUMENTS

| 4,446,858 | 5/1984 | Verter .......................................... 602/4 |
| 5,188,587 | 2/1993 | McGuire et al. ........................... 602/4 |

Primary Examiner—Kim M. Lewis
Attorney, Agent, or Firm—Donald E. Nist

[57] ABSTRACT

The improved shoulder brace of the present invention includes a support having a cup-shaped central portion adapted to receive and support a human shoulder, a front portion adapted to extend over the chest area of a person wearing the brace, a lower portion depending below the central portion and adapted to encircle and support the upper portion of the arm adjacent the shoulder, and a rear portion adapted to extend over the scapular area adjacent the shoulder. The support can be a single piece of flexible sheet material, with or without padding, and preferably is porous, or can be separate pieces interconnected to form a unitary whole. Preferably, the support is of a porous mesh material or an elastomeric material with spaced openings. The brace also includes a first elongated strap connected at one end to the rear portion of the support and bearing on its opposite free end a conector which releasably secures to a connector on the front portion of the support for releasably and adjustably holding the brace around the torso. A second strap has one end connected to the lower portion of the support and an opposite free end bearing a connector which releasably secures to a connector on the lower portion, thus enabling the lower portion to be releasably secured around the arm to be supported.

8 Claims, 4 Drawing Sheets

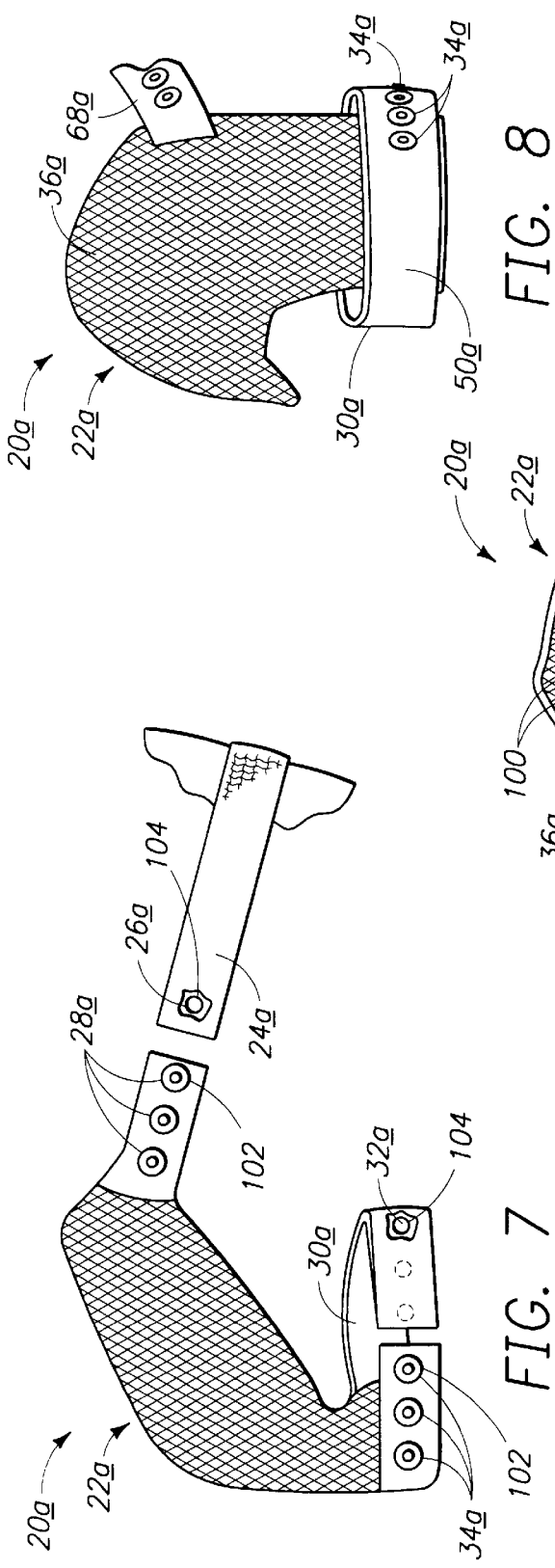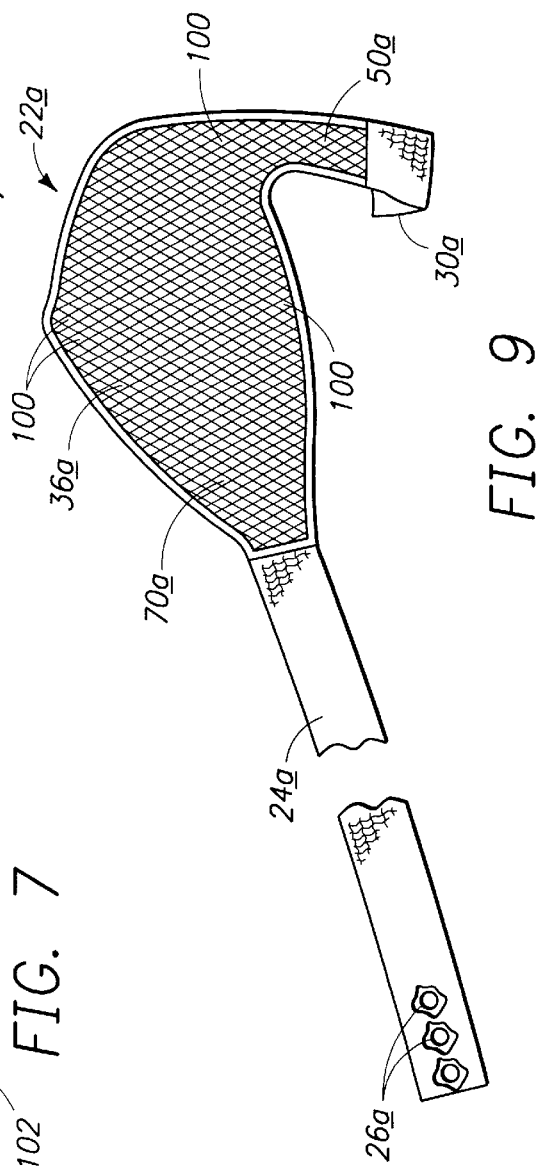

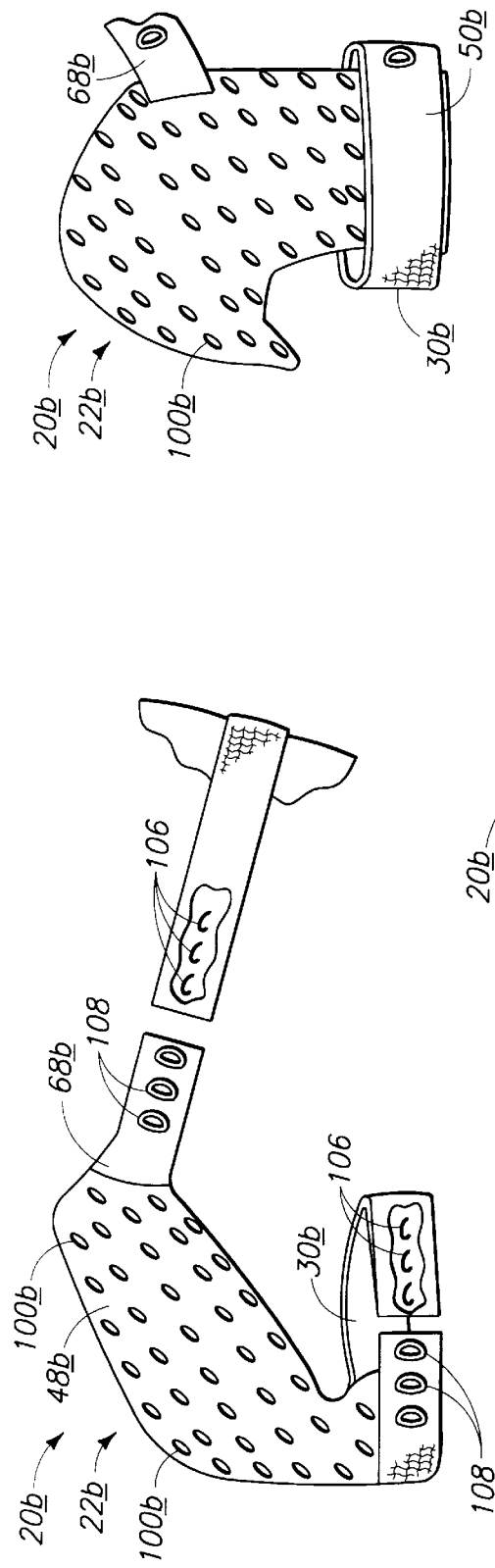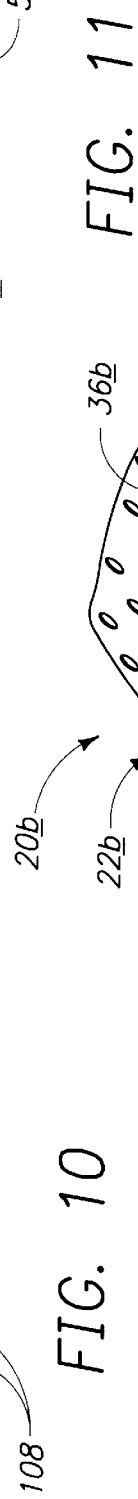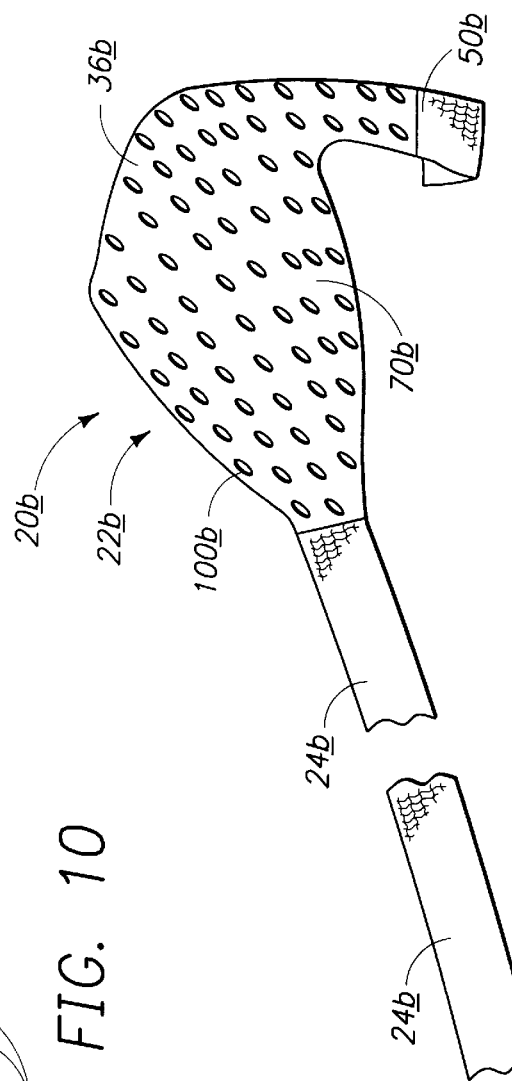

HUMAN SHOULDER BRACE

BACKGROUND OF THE INVENTION

1. Field of the Invention

The present invention generally relates to braces and more particularly to an improved brace which supports the human shoulder and/or arm in case of an injury or for support for sporting purposes and the like.

2. Prior Art

Various types of shoulder braces have been designed and utilized to immobilize and support injured shoulders and/or arms. Such braces usually are relatively expensive, cumbersome and difficult to don and remove. In many cases the user requires the assistance of another person in order to don and adjust the brace for maximum comfort and effectiveness. Moreover, most such braces are relatively thick and/or heavy and are unsuitable for use in hot weather.

There are also occasions when it is desireable to protect arms and shoulders against trauma. For example, when shooting powerful rifles which have substantial recoil, bruising of the shoulder and arm can easily occur. The same danger is encountered during participation in shotgun sports such as skeet and trap shooting and when hunting using shotguns and rifles. Devices capable of protecting the shoulder and arm against impact injury during these activities would be desireable. Such devices should be light in weight, capable of being easily put on and taken off by the user and of being adjusted when worn for maximum comfort and support. Such devices should be durable, inexpensive and porous and preferably should be cushioned to minimize perceived impact with the shoulder and arm.

SUMMARY OF THE INVENTION

The shoulder and arm brace of the present invention satisfies all the foregoing needs. The brace is inexpensive, durable, light in weight and can be made sufficiently porous to be comfortably worn even in hot weather. Moreover, the brace can be easily donned and removed by the user without assistance from a second party. In addition, the brace can be adjusted by the user to maximize the effectiveness of the brace to protect the shoulder and arm and to fit precisely in place.

The improved human shoulder and arm brace of the present invention comprises a support preferably formed of either a single flexible sheet or a composite of interconnected sheets of material such as cloth, elastomeric material or the like which can be sufficiently porous to prevent sweating of the protected area when worn. The support includes a central cup-shaped portion which is adapted to closely overlie the shoulder, a front portion integral with or connected thereto which is adapted to overlie a portion of the chest area of the user, a lower depending portion integral with or connected to the central portion and which is adapted to encircle the upper arm of the user and a rear portion which is integral with or connected to the central portion and which is adapted to overlie the scapular area of the shoulder and back portion of the torso of the wearer. Said rear portion of the support preferably is generally triangular in shape, narrowing toward the spine and can be formed of a single sheet or composite sheet of material or a plurality, preferably three, of interconnected strips joined together at about the apex thereof. This latter configuration maximizes the close fit of the rear portion to the scapular area of the wearer, regardless of the size and shape of the wearer.

The support also includes a first elongated strap, one end of which is connected to the rear portion of the support, preferably at the apex thereof, and the opposite free end of which strap bears a connector which mates with a connector on the front portion of the support in order to releasably and adjustably secure the brace around the torso of the wearer of the brace.

The brace further includes a second elongated strap having one end connected to the lower portion of the support and the opposite free end of which strap bears a connector which releasably mates with a connector secured to the lower portion of the support, preferably in a forwardly projecting position for easy manipulation by the wearer of the brace. This second strap projects about horizontally for encircling the lower support to adjustably and releasably secure it in place around the upper portion of the arm of the wearer of the brace and helping to securely fix the brace in place on the wearer while also protecting the upper arm against trauma.

Thus, the brace is simple to use and is efficient. One size can fit human torsos of various sizes. The brace is neat and attractive in appearance and can be easily carried and stored.

Further features of the improved brace of the present invention are set forth in the following detailed description and accompanying drawings.

DRAWINGS

FIG. 7 is an enlarged, schematic, fragmentary front perspective view, partly broken away, of a second preferred embodiment of the improved brace of the present invention;

FIG. 8 is an enlarged, schematic, fragmentary side perspective view, partly broken away, of the brace of FIG. 7;

FIG. 9 is an enlarged, schematic, fragmentary rear perspective view, partly broken away, of the brace of FIG. 7;

FIG. 10 is an enlarged, schematic, fragmentary front perspective view, partly broken away, of a third preferred embodiment of the improved shoulder brace of the present invention;

FIG. 11 is an enlarged, schematic, fragmentary side perspective view, partly broken away, of the brace of FIG. 10; and, FIG. 12 is an enlarged, schematic, fragmentary rear perspective view, partly broken away, of the brace of FIG. 10.

DETAILED DESCRIPTION OF THE EMBODIMENTS OF THE INVENTION

FIGS. 1–6

Figure 1:
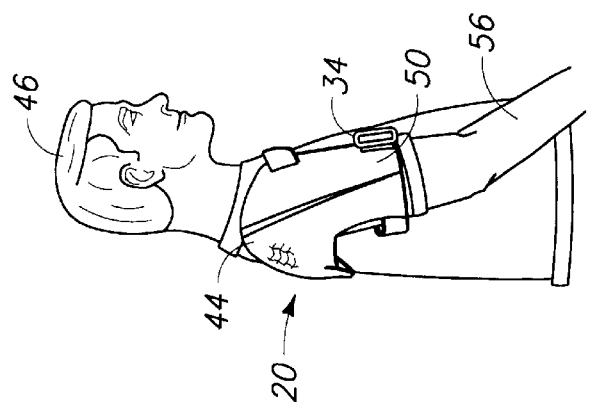
FIG. 1 is a schematic front elevation of a first preferred embodiment of the improved human shoulder brace of the present invention, shown being worn.

Now referring more particularly to FIGS. 1 through 6 of the drawings, a first preferred embodiment of the improved shoulder and arm brace of the present invention is schematically depicted therein. Thus, brace 20 is shown, which comprises, in combination, a support 22, a first strap 24, a first set of connectors 26 and 28, a second strap 30 and a second set of connectors 32 and 34.

Figure 3:
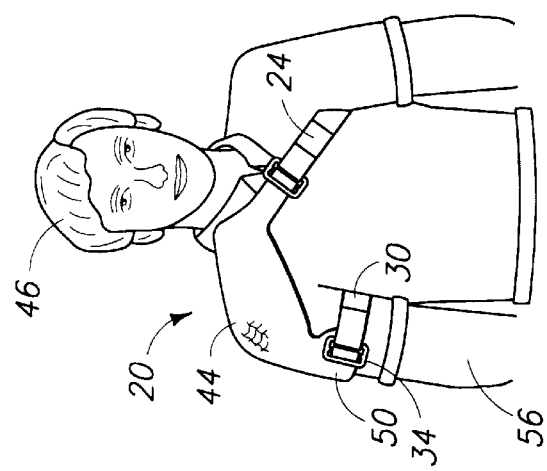
FIG. 3 is a schematic side elevation of the brace of FIG. 1, shown being worn.
Figure 5:
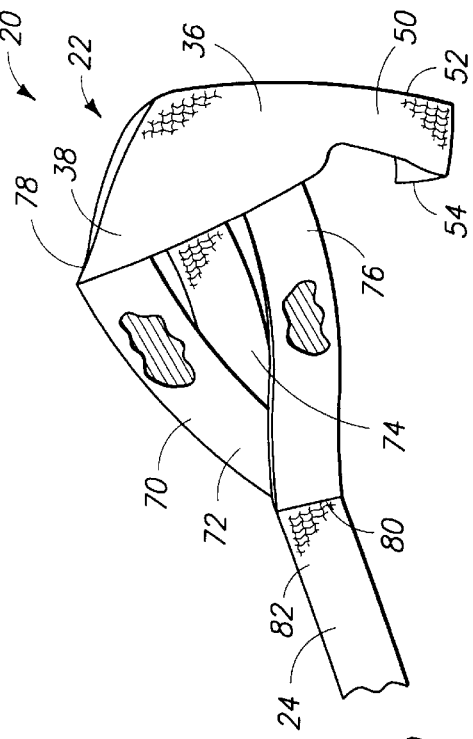
FIG. 5 is an enlarged, schematic, fragmentary side perspective view, partly broken away, of the brace of FIG. 1.

Support 22 comprises a cup-shaped central portion 36, best shown in FIGS. 3 and 5, which can be formed, for example of a sheet 38 of flexible resilient cushioning material having an outer layer 40 of durable material and an inner layer 42 of cushioning material. The remainder of support 22 can be formed of the same or similar material. Central portion 36 is adapted to cup and support the main portion of the shoulder 44 of the wearer 46 of brace 20. Support 22 also includes a front portion 48 integral with or connected to central portion 36 and extending around the front of the shoulder 44 of the wearer 46, as shown in FIG. 1, and unto the front of the chest portion of the wearer 46.

Figure 4:
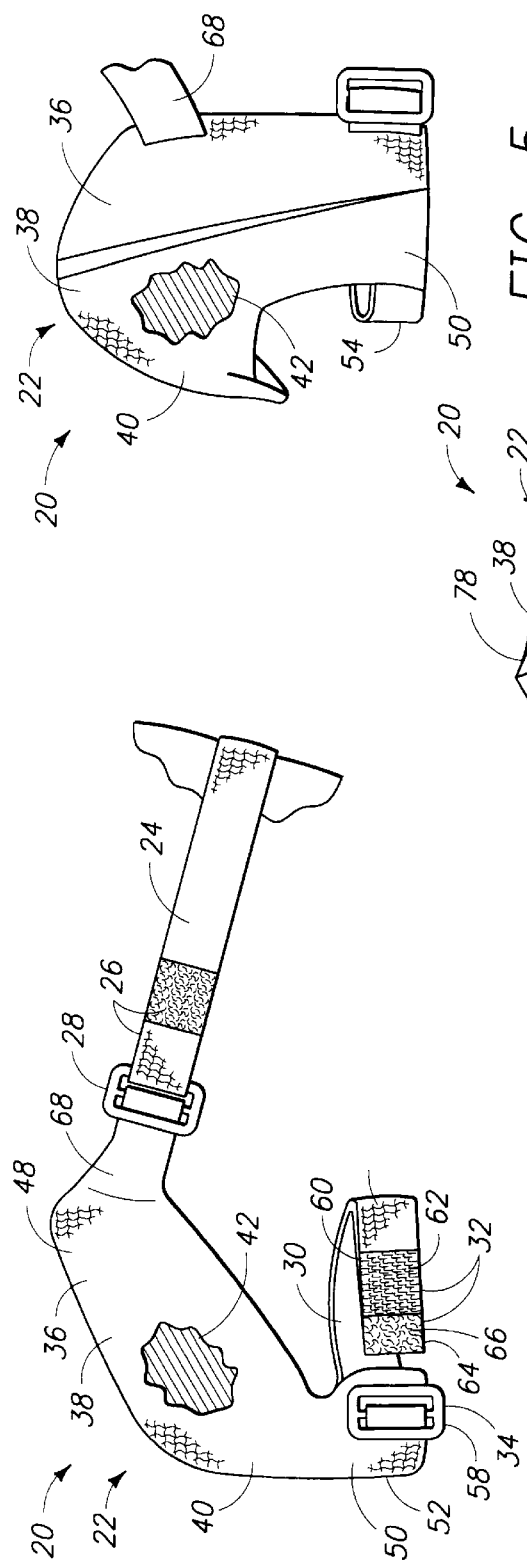
FIG. 4 is an enlarged, schematic, fragmentary front perspective view, partly broken away, of the brace of FIG. 1.

Support 22 further includes a lower portion 50 which depends from the lower end of central portion 36 and is integral therewith or connected thereto. Lower portion 50 is split vertically into two sections 52 and 54 so that the upper arm 56 of wearer 46 can easily inserted into portion 50. Connector 34 is connected to and projects outwardly from the front end of section 52 of lower portion 50 while strap 30 is attached at one end thereof in a horizontal direction to the exterior of section 54 of portion 50. With this arrangement, lower portion 50 can be releasably and adjustably secured by the wearer of brace 20, without assistance, around the upper portion of arm 56 to hold brace 20 in place on wearer 46. In this regard, connector 32 carried on the free end of strap 30 releasably mates with connector 34. Connector 34, as shown in FIG. 4, comprises a loop or buckle 58 while connector 32 comprises a strip 60 of hooks 62 on the front surface of strap 30 adjacent to a strip 64 of hook receptors 66 on said surface. Strap 30 can be fed through buckle or loop 58 and back on itself and then releasably fixed in place via hooks 62 and hook receptors 66. Since buckle 58 is on the front of lower portion 50, this releasable closing of portion 50 can easily be carried out by wearer 46 without assistance.

Central portion 36, as previously mentioned, has front portion 48 of support 22 integral therewith or connected thereto and extending around the front of the shoulder of wearer 46 so as to overlie a portion of the chest area of wearer 46. Front portion 48 includes a narrow extension 68 directed diagonally downwardly and bearing connector 28 on the front surface thereof. Connector 28 is similar to connector 34.

Figure 2:
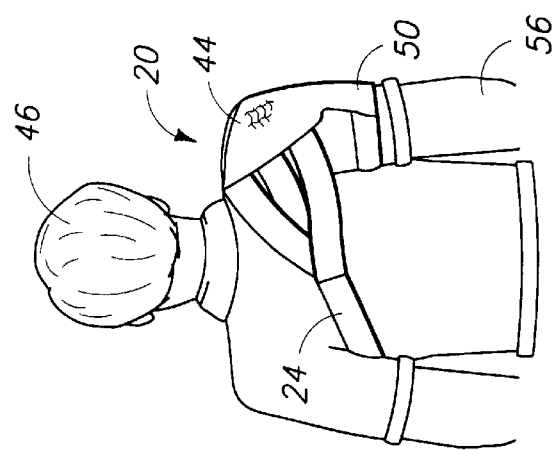
FIG. 2 is a schematic rear elevation of the brace of FIG. 1, shown being worn.
Figure 6:
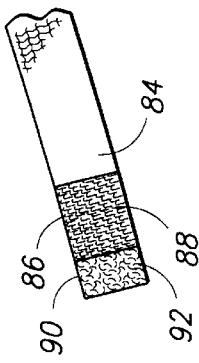
FIG. 6 is an enlarged, schematic, fragmentary rear perspective view, partly broken away, of the brace of FIG. 1.

Support 22 also includes a rear portion 70 integral with or connected to central portion 36 and having a generally triangular configuration with the apex thereof extending diagonally downwardly toward the spine (not shown) of wearer 46. Preferably, as shown in FIGS. 2 and 6, portion 70 comprises three separate strips 72, 74 and 76 of material, each joined separately at one end thereof to the rear end 78 of central portion 36 and converging and being joined together adjacent apex 80 of rear portion 70. Strips 72, 74 and 76 permit a better conforming of rear portion 70 to the configuration of the back of wearer in the scapular region, thus resulting in a more comfortable and better fit for brace 20 on wearer 46.

End 82 of strap 24 is connected to apex 80 while the opposite free end 84 of strap 24 is adapted to wrap around the upper portion of the torso of wearer 46, as shown in FIG. 2, passing under the arm opposite that which bears portion 50 and is releasably and adjustably secured at the front of wearer 46, as shown in FIGS. 1 and 4. Free end 84 of strap 24 bears on the front surface thereof a strip 86 of hooks 88 and adjacent thereto a strip 90 of hook receptors 92 so that free end 84 can be passed through buckle connector 28 and looped back on itself to releasbly connect hooks 88 and receptors 92 to hold brace 20 securely in place. This releasable connection can be carried out by wearer 46 without any assistance from a second party. Similarly, straps 24 and 30 can be released by wearer 46 when it is desired to remove brace 20. Because wearer 46 can completely adjust brace 20 while it is being worn, comfort and proper fit, with maximum shoulder and upper arm support and protection are assured. Accordingly, brace 20 has improved characteristics over the prior art devices.

FIGS. 7–9

A second preferred embodiment of the improved brace of the present invention is schematically depicted in FIGS. 7–9. Thus, brace 20*a* is shown. Components similar to those of brace 20 bear the same numerals, but are succeeded by the letter "a".

Brace 20*a* is substantially identical to brace 20, except as follows:

a) Support 22*a* comprises a single sheet of woven stretchable material which is flexible and resilient and fabricated of elastomer such as rubber, rubber-like plastic or of textile material having characteristics similar to an elastomer. The sheet has a plurality of small closely spaced openings 100 in a regular pattrn throughout which assures maximum comfort and fit as well as support for brace 20*a*.

b) Connectors 26*a*, 28*a*, 32*a* and 34*a* comprise metallic or plastic buttons 102 and snaps 104.

Brace 20*a* has the other advantages of brace 20.

FIGS. 10–12

A third preferred embodiment of the improved brace of the present invention is schematically depicted in FIGS. 10–12. Thus, brace 20*b* is shown. Components thereof similar to those of brace 20 and/or brace 20*a* bear the same numerals but are succeeded by the letter "b".

Brace 20*b* is substantially identical to brace 20 except as follows:

a) Connectors 26*b*, 28*b*, 32*b* and 34*b* comprise a spaced series of metallic or plastic hooks 106 and loops 108.

b) Support 22*b* is a single sheet of woven textile material or the like having large spaced openings 100*b* therein for optimal comfort for brace 20*b*.

Brace 20*b* has the other advantages of brace 20.

Various other modifications, changes, alterations and additions can be made in the brace of the present invention, its components and their parameters. All such modifications, changes, alterations and additions as are within the scope of the appended claims form part of the present invention.

Prior Art Statement

A preliminary patentability search has been made on the subject matter of the present invention. However, no relevant patents have been located during the search of the prior art. Accordingly, Applicant believes that the present claimed invention is patentable.

What is claimed is:

1. An improved shoulder brace for use by humans, said brace comprising, in combination:

a) a support comprising a cup-shaped central portion adapted to receive and support a human shoulder, a front portion connected to said central portion and adapted to extend across the front of the chest of the human adjacent the shoulder, a lower portion connected to and depending from said central portion and adapted to encircle and support the upper arm of the human adjacent the shoulder, and a rear portion connected to said central portion and extending rearwardly thereof and adapted to extend over the scapula of the human adjacent the shoulder, said rear portion of said support being generally triangular and comprising three separate interconnected elongated strips adapted to conform said rear portion to the contours of the scapular area of the human;

b) a first elongated strap having a first end connected to said rear portion of said support and an opposite free end;

c) a first set of connectors disposed on said free end of said first strap and on said front portion of said support for permitting the human to releasably and adjustably connect said shoulder brace in an operative position around the human without assistance;

d) a second elongated strap having a first end connected to said lower portion of said support and an opposite free end; and, e) a second set of connectors on said lower portions of said support and on said free end of said second strap for permitting the human to releasably and adjustably secure said lower portion of said support into an operative shoulder- and arm-supporting position without assistance.

2. The improved shoulder brace of claim 1 wherein said connector of said second set which is on said lower portion of said support is on the front thereof to facilitate self-securing by the wearer of said brace of said lower portion into said operative shoulder- and arm-supporting position.

3. The improved shoulder brace of claim 2 wherein said central portion of said support is padded and adapted to conform to the shape of said shoulder.

4. The improved shoulder brace of claim 3 wherein said rear portion of said support is padded.

5. The improved shoulder brace of claim 1 wherein at least one of said central portion and said rear portion of said support comprises porous flexible sheet material.

6. The improved shoulder brace of claim 5 wherein said sheet material comprises a porous elastomeric material.

7. The improved shoulder brace of claim 6 wherein said connectors comprise mating hooks and hook receptors.

8. The improved shoulder brace of claim 1 wherein said connectors comprise mating buttons and snaps.

\* \* \* \* \*